US00PP22987P2

(12) United States Plant Patent
Danziger

(10) Patent No.: US PP22,987 P2
(45) Date of Patent: Aug. 21, 2012

(54) ***CALIBRACHOA* PLANT NAMED 'DANOA60'**

(50) Latin Name: ***Calibrachoa* sp.**
Varietal Denomination: DANOA60

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/066,979

(22) Filed: Apr. 29, 2011

(51) Int. Cl.
*A01H 5/00* (2006.01)

(52) U.S. Cl. ..... Plt./413

(58) Field of Classification Search ..... Plt./413
See application file for complete search history.

*Primary Examiner* — June Hwu
*Assistant Examiner* — Louanne Krawczewicz Myers
(74) *Attorney, Agent, or Firm* — Cassandra Bright

(57) ABSTRACT

A new and distinct *Calibrachoa* cultivar named 'DANOA60' is disclosed, characterized by large light blue flowers with a yellow throat, early and abundant flowering. The new variety has a mounded growth habit and moderate vigor. The new variety is a *Calibrachoa*, normally produced as an outdoor garden or container plant.

2 Drawing Sheets

Latin Name of the genus and species: *Calibrachoa* sp.
Variety denomination: 'DANOA60'.

BACKGROUND OF THE INVENTION

The new *Calibrachoa* cultivar is a product of a planned breeding program conducted by the inventor, Gavriel Danziger, in Moshav Mishmar Hashiva, Israel. The objective of the breeding program was to produce new *Calibrachoa* varieties for ornamental commercial applications. The cross resulting in this new variety was made during November 2008.

The seed parent is the unpatented, proprietary seedling variety referred to as *Calibrachoa* sp. 'Ca-2154' The pollen parent is unknown, as the crossing resulting in 'DANOA60' was an open pollination, with unidentifiable pollen parents. The new variety was discovered in April 2009 by the inventor in a group of seedlings resulting from the 2008 crossing, in a research greenhouse in Moshav Mishmar Hashiva, Israel.

Asexual reproduction of the new cultivar 'DANOA60' by vegetative cuttings was first performed at a research greenhouse in Moshav Mishmar Hashiva, Israel in April 2009 and has shown that the unique features of this cultivar are stable and reproduced true to type in successive generations.

SUMMARY OF THE INVENTION

The cultivar 'DANOA60' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOA60' These characteristics in combination distinguish 'DANOA60' as a new and distinct *Calibrachoa* cultivar:

1. Large flower size
2. Early flowering.
3. Light blue flower with a yellow throat.
4. Mounded plant habit Plants of the new cultivar 'DANOA60' are similar to plants of the seed parent, *Calibrachoa* sp. 'CA-2154' in most horticultural characteristics, however, plants of the new cultivar 'DANOA60' produce larger flowers of a different color, and more branches per plant.

COMMERCIAL COMPARISON

Plants of the new cultivar 'DANOA60' are comparable to the variety *Calibrachoa* 'DANOA35' U.S. Plant Pat. No. 19,779. The two *Calibrachoa* varieties are similar in most horticultural characteristics, including a mounded plant habit. The new variety 'DANOA60' differs in having different color flowers, larger flowers and less branching per plant.

Plants of the new cultivar 'DANOA60' can also be compared to the commercial variety *Calibrachoa* 'DANCALMIDBLU' U.S. Plant Pat. No. 18,123. These varieties are similar in most horticultural characteristics, however 'DANOA60' has darker blue colored flowers and a slightly less compact plant habit. Additionally, plants of 'DANOA60' produce larger flowers than 'DANCALMIDBLU'.

BRIEF DESCRIPTION OF THE PHOTOGRAPHS

Figure 1:
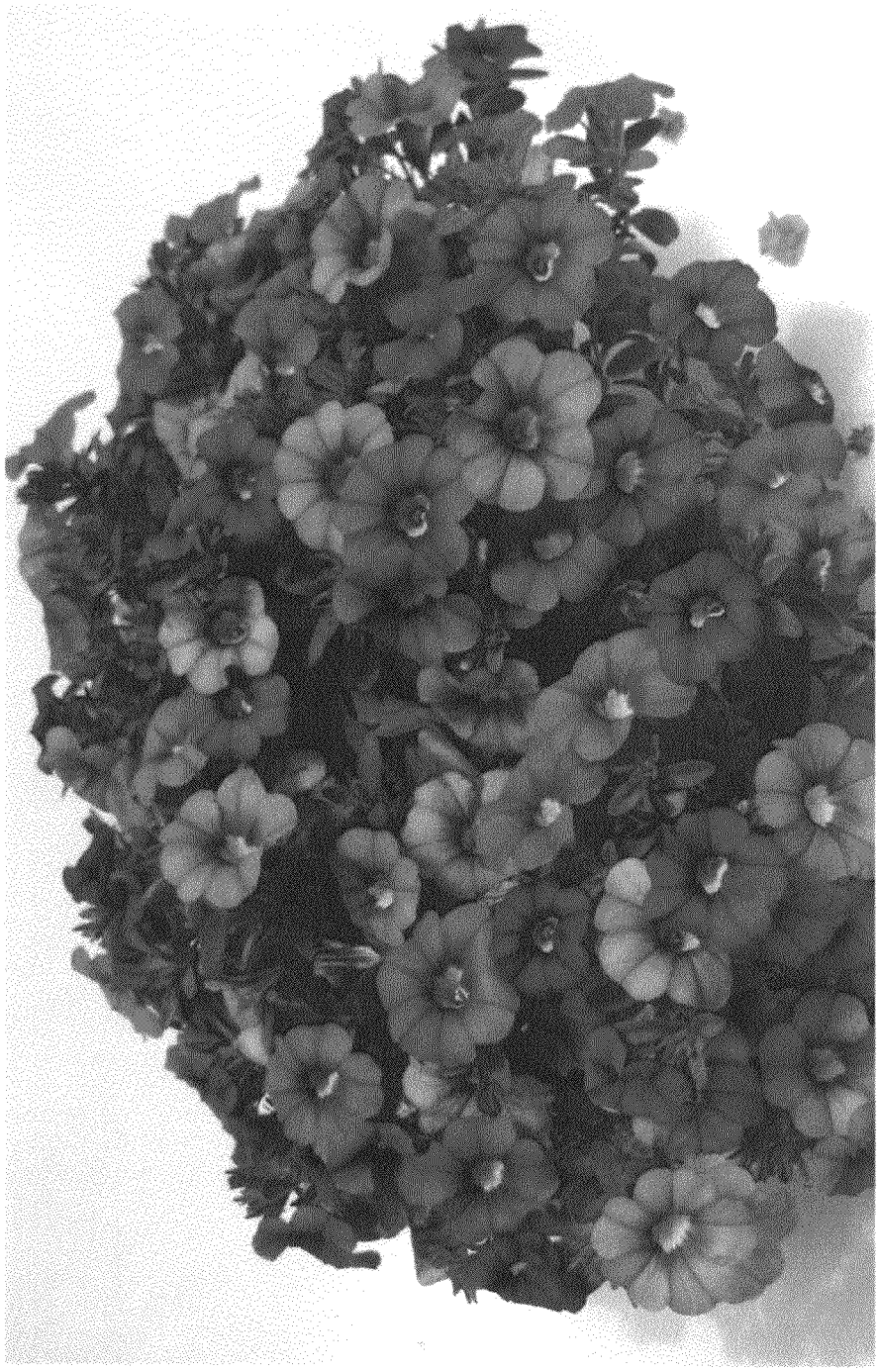

The accompanying photograph in FIG. 1 illustrates in full color a typical plant of 'DANOA60' grown in a greenhouse, in a 13 cm basket. Age of the plant photographed is approximately 3 months from a rooted cutting.

Figure 2:
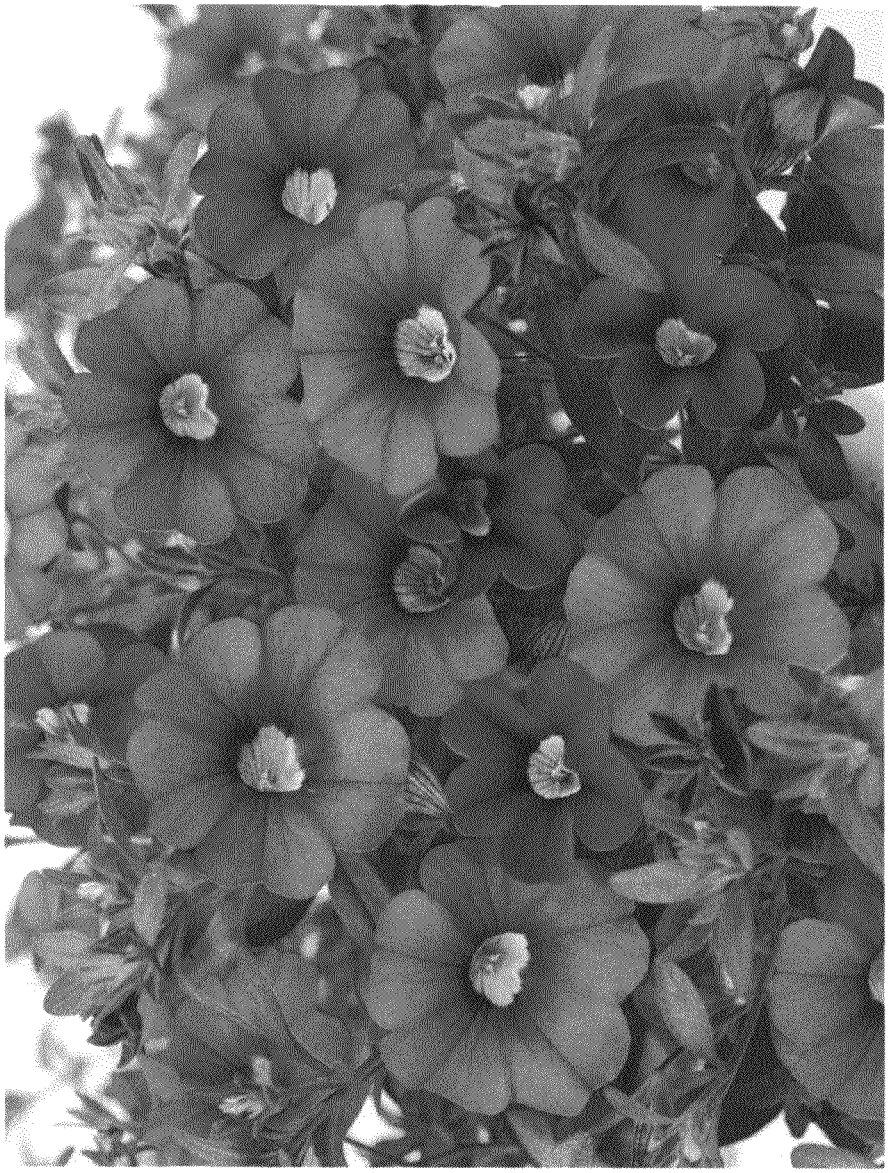

FIG. 2 illustrates in full color a close up of a typical bloom of 'DANOA60'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DANOA60' plants grown in a greenhouse, and moved outdoors during Spring in Moshav Mishmar Hashiva, Israel. The growing temperature ranged from 10° C. to 35° C. during the day and from 7° C. to 20° C. during the night. General light conditions are bright, normal sunlight. Measurements and numerical values represent averages of typical plant types. Plants are approximately 60 days old from a rooted cutting. Botanical classification: *Calibrachoa* sp. 'DANOA60'.

PROPAGATION

Time to initiate roots: About to 10 to 12 days at approximately 25° C.
Root description: Fine, fibrous.

PLANT

Growth habit: Mounded.
Pot site of plant described: 13 cm.
Age of plant described: Approximately 60 days from a rooted cutting.
Height: Approximately 12 cm., to top of highest flower.
Plant spread: Approximately 35 cm.
Growth rate: Moderate.
Branching characteristics: Moderately free branching.
Length of primary lateral branches: Approximately 17 cm.
Diameter of lateral branches: Approximately 0.2 cm.
Quantity of primary lateral branches: Approximately 20.
Characteristics of primary lateral branches:
*Form*.—Round.
*Diameter*.—Approximately 0.2 cm.
*Color*.—Near RHS Green 137A, heavily flushed Red-Purple 72A.
*Texture*.—Pubescent.
*Strength*.—Medium.
Internode length: Average 2-3 cm.

FOLIAGE

Leaf:
*Arrangement*.—Opposite.
*Quantity*.—Approximately 20 per lateral branch.
*Average length*.—Average 2.8 cm.
*Average width*.—Average 1.1 cm.
*Shape of blade*.—Oblanceolate.
*Apex*.—Obtuse.
*Base*.—Acute.
*Margin*.—Entire.
*Texture of surfaces*.—Slightly pubescent both upper and lower surfaces.
*Angle of attachment*.—45°.
*Aspect*.—Flat.
*Color*.—Young foliage upper side: Near RHS Green 137 B. Young foliage under side: Near RHS Green 137 C. Mature foliage upper side: Near RHS Green 137 A. Mature foliage under side: Near RHS Yellow-Green 147 B.
*Venation*.—Type: Pinnate. Venation color upper side: Near RHS Green 137 A. Venation color under side: Near RHS Yellow-Green 147 B.
*Petiole*.—Not present.

FLOWER

Natural flowering season: All year round in moderate climates.
Days to flowering from rooted cutting: Approximately 4 weeks.
Inflorescence and flower type and habit: Terminal, Single, Salverform.
Rate of flower opening: 1 to 3 days from bud to fully opened flower.
Flower longevity on plant: About 3 to 6 days.
Approximate quantity of flowers per plant: 50-60 at 60 days old.
Persistent or self-cleaning: Self-cleaning.
Fragrance: None.
Bud:
*Shape*.—Tubular.
*Length*.—1.2-1.5 cm.
*Diameter*.—0.5 cm.
*Color*.—At proximal end Near RHS Yellow-Green 151D. At distal end Near RHS Violet 85C.
*Texture*.—Velvety.
Flower size:
*Diameter*.—3.5 to 4.0 cm.
*Length*.—2.0 to 2.5 cm.
*Flower tube diameter at distal end*.—1 to 1.5 cm.
*Flower tube diameter at proximal end*.—0.3 cm.
*Flower tube length*.—Approximately 1.5 to 1.9 cm.
Petals:
*Length from throat*.—1.5 to 1.8 cm.
*Width*.—2 to 2.2 cm.
*Quantity*.—4 fused petals.
*Shape*.—Petals fused into salverform flower shape, individual petals somewhat deltate.
*Texture*.—Smooth, all surface.
*Apex*.—Retuse.
*Margin*.—Entire.
*Color*.—When opening: Upper surface: Near RHS Violet N 88A. Lower surface: Near RHS Violet N 88C. Fully opened: Upper surface: Near RHS Violet-Blue N89D. Lower surface: Near RHS Violet N 88D. Flower throat (inside): Near RHS Green-Yellow 1C. Flower throat, vein: Near RHS Violet N 87A. Flower tube (outside): Neat RHS Yellow 3C. Flower tube, vein: Near RHS Violet N 87A. Petal color, fading to: Near RHS Violet N 87C, all petal surfaces.
Calyx/sepals:
*Quantity per flower*.—5.
*Shape*.—Lanceolate.
*Length*.—Approximately 1.5 cm.
*Width*.—Approximately 0.4 cm.
*Apex*.—Acute.
*Base*.—Cuneate.
*Margin*.—Entire.
*Texture*.—Pubescent all surfaces.
*Color*.—Upper surface: Near RHS Yellow-Green 146A. Lower surface: Near Green 137B.
Peduncle:
*Length*.—Average 1.5 to 2.0 cm.
*Diameter*.—0.1 cm.
*Color*.—Near RHS Yellow-Green 144A.
*Texture*.—Lightly pubescent.
*Orientation*.—Straight, 45° angle from stem.

REPRODUCTIVE ORGANS

Stamens:
*Stamens*.—Number: 5. Filament length: 1 cm.

Anthers:

*Length*.—0.1 cm.

*Shape*.—Round.

*Color*.—Near RHS Yellow 11A.

*Pollen*.—Color: Near RHS Yellow 12A. Quantity: abundant.

Pistil:

*Number*.—1.

*Length*.—0.5 to 0.8 cm.

*Style*.—Length: 0.7 cm. Color: Near RHS Green 143C.

*Stigma*.—Shape: round. Color: Near RHS Green 139C. Ovary Color: Near RHS Green 139A.

OTHER CHARACTERISTICS

Seeds and fruits: Not observed.

Disease/pest resistance: Neither resistance nor susceptibility to pathogens and pests common to *Calibrachoa* have been observed.

Temperature tolerance: The new variety tolerates temperatures between 0 to 40° C.

What is claimed is:

1. A new and distinct cultivar of *Calibrachoa* plant named 'DANOA60' as herein illustrated and described.

* * * * *